(12) United States Patent
Ergler et al.

(10) Patent No.: US 10,761,221 B2
(45) Date of Patent: Sep. 1, 2020

(54) X-RAY DETECTOR COMPRISING A CONVERTER ELEMENT WITH REWIRING UNIT

(71) Applicant: Siemens Healthcare GmbH, Erlangen (DE)

(72) Inventors: Thorsten Ergler, Erlangen (DE); Harald Geyer, Bubenreuth (DE); Christian Schroeter, Bamberg (DE); Justus Tonn, Forchheim (DE); Jan Wrege, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 134 days.

(21) Appl. No.: 15/919,377

(22) Filed: Mar. 13, 2018

(65) Prior Publication Data
US 2018/0267181 A1 Sep. 20, 2018

(30) Foreign Application Priority Data

Mar. 15, 2017 (EP) ..................... 17161126

(51) Int. Cl.
*G01T 1/24* (2006.01)
*G01T 1/29* (2006.01)
(Continued)

(52) U.S. Cl.
CPC .............. *G01T 1/241* (2013.01); *A61B 6/035* (2013.01); *A61B 6/4014* (2013.01);
(Continued)

(58) Field of Classification Search
CPC ... A61B 6/4233; A61B 6/4241; A61B 6/4266; A61B 6/4275
See application file for complete search history.

(56) References Cited

U.S. PATENT DOCUMENTS 9,651,686 B2 * 5/2017 Lee ........................... G01T 1/24
2003/0016779 A1 1/2003 Pohan et al.
(Continued)

FOREIGN PATENT DOCUMENTS

DE 10138913 A1 3/2003
DE 102012213410 B3 9/2013
(Continued)

OTHER PUBLICATIONS

German Office Action dated Aug. 28, 2017, Application No. 2017P03424EP Patent No. 17161126.2-1559.

*Primary Examiner* — David P Porta
*Assistant Examiner* — Mamadou Faye
(74) *Attorney, Agent, or Firm* — Harness, Dickey & Pierce, P.L.C.

(57) ABSTRACT

A counting x-ray detector includes a converter element, a rewiring unit and an evaluation unit including pixel electrodes. In an embodiment, the converter element includes a first electrode on a surface facing away from the evaluation unit and a pixelated second electrode having a plurality of electrode elements on a surface facing toward the evaluation unit. The rewiring unit is on a surface of the converter element facing toward the evaluation unit. First contacts of electrically conductive connections between the electrode elements and the pixel electrodes are provided on a surface of the rewiring unit and include a first areal distribution; and second such contacts are provided on a surface of the rewiring unit, including a relatively smaller second areal distribution. An areal extent of the evaluation unit is relatively smaller than an areal extent of the converter element.

26 Claims, 5 Drawing Sheets

(51) Int. Cl.
  *A61B 6/03* (2006.01)
  *A61B 6/00* (2006.01)
  *H01L 23/00* (2006.01)
  *H01L 27/146* (2006.01)
  *H01L 31/0224* (2006.01)
  *H01L 31/115* (2006.01)

(52) U.S. Cl.
  CPC ............ *A61B 6/4208* (2013.01); *G01T 1/243* (2013.01); *G01T 1/247* (2013.01); *G01T 1/2928* (2013.01); *H01L 24/10* (2013.01); *H01L 27/14676* (2013.01); *H01L 31/0224* (2013.01); *H01L 31/115* (2013.01); *H01L 2224/16221* (2013.01)

(56) References Cited

U.S. PATENT DOCUMENTS

| | | | |
|---|---|---|---|
| 2004/0017224 A1* | 1/2004 | Tumer | H03F 3/087 327/51 |
| 2006/0092615 A1* | 5/2006 | Burdick, Jr. | H05K 1/147 361/803 |
| 2007/0280409 A1* | 12/2007 | Konno | G01T 1/249 378/19 |
| 2012/0133001 A1 | 5/2012 | Tkaczyk et al. | |
| 2012/0211663 A1* | 8/2012 | Kim | H01L 27/14632 250/370.13 |
| 2012/0223241 A1 | 9/2012 | Kim et al. | |
| 2015/0260856 A1 | 9/2015 | Dierre et al. | |
| 2015/0312501 A1* | 10/2015 | Fahim | H01L 27/14661 348/294 |
| 2016/0240584 A1* | 8/2016 | El-Hanany | H01L 27/14696 |
| 2017/0176608 A1 | 6/2017 | Ergler et al. | |
| 2017/0192110 A1* | 7/2017 | Steadman Booker | G01T 1/244 |

FOREIGN PATENT DOCUMENTS

| | | |
|---|---|---|
| DE | 102015225774 B3 | 6/2017 |
| WO | WO-2015012866 A1 | 1/2015 |
| WO | WO-2016046014 A1 | 3/2016 |

* cited by examiner

X-RAY DETECTOR COMPRISING A CONVERTER ELEMENT WITH REWIRING UNIT

PRIORITY STATEMENT

The present application hereby claims priority under 35 U.S.C. § 119 to European patent application number EP 17161126.2 filed Mar. 15, 2017, the entire contents of which are hereby incorporated herein by reference.

FIELD

At least one embodiment of the invention generally relates to an x-ray detector including a converter element with a rewiring unit embodied on a surface of the converter element facing toward the evaluation unit, and/or to a medical device and/or production method therefor.

BACKGROUND

Counting direct-converting x-ray detectors or integrating indirect-converting x-ray detectors can be used in x-ray imaging, for example in computed tomography, angiography or radiography.

In direct-converting x-ray detectors, the x-ray radiation or the photons can be converted into electrical pulses via a suitable converter material. Examples of suitable converter material are CdTe, CZT, CdZnTeSe, CdTeSe, CdMnTe, InP, $TlBr_2$, $HgI_2$, GaAs, or other materials. The electrical pulses, for example voltage pulses, are interpreted by evaluation electronics, for example an integrated circuit (Application Specific Integrated Circuit (ASIC)), in an evaluation unit. In counting x-ray detectors, incident x-ray radiation is measured by counting the electrical pulses triggered due to the absorption of x-ray photons in the converter material. The height of the electrical pulse is generally proportional to the energy of the absorbed x-ray photon. This enables spectral information to be extracted by comparing the height of the electrical pulse with a threshold value. The evaluation unit can be connected to a carrier unit, for example a ceramic substructure, such that an increased mechanical stability can be achieved and a rewiring of the signal connections to downstream signal processing units can be provided. In order to counteract the incidence of scattered x-ray photons, an antiscatter grid can be embodied on the side of the converter element facing toward the radiation source.

DE 10 2012 213 410 B3 discloses a direct-converting x-ray radiation detector that has at least one electrode deposited on a semiconductor. The at least one electrode and the semiconductor are connected in an electrically conducting manner, the at least one electrode being embodied as transparent and electrically conductive.

A detector module for x-ray computed tomography apparatus is known from DE 101 38 913 A1, wherein a sensor array comprising a plurality of sensor elements is mounted on a front side of a printed circuit board. In order to increase the accuracy of the detector, it is provided according to the invention that at least one heating element is provided on the back side of the printed circuit board facing away from the sensor array for the purpose of heating the sensor array and a control electronics circuit arranged close to the heating element for the purpose of controlling the heating element.

SUMMARY

The inventors have discovered that an underlying problem is that the evaluation unit and the converter element extend over a substantially equal-sized area (areal extent) in order to obtain a mechanically stable stack structure. Consequently, the costs are high, since the costs of the evaluation unit are dependent on the areal extent of the evaluation unit.

At least one embodiment of the invention discloses an x-ray detector, a medical device and a method for producing an x-ray detector which enable a cost-effective and mechanically stable x-ray detector to be realized.

At least one embodiment of the invention is directed to an x-ray detector; a medical device; and a method.

At least one embodiment of the invention relates to a counting x-ray detector having a stack arrangement comprising a converter element, a rewiring unit and an evaluation unit. The converter element has a first electrode on a surface facing away from the evaluation unit and a pixelated second electrode having a plurality of electrode elements on a surface facing toward the evaluation unit. The evaluation unit has pixel electrodes. The rewiring unit is embodied on a surface of the converter element facing toward the evaluation unit, first contacts of electrically conductive connections between the electrode elements and the pixel electrodes being provided on a surface of the rewiring unit facing toward the converter element and having a first areal distribution, and second contacts of the electrically conductive connections between the electrode elements and the pixel electrodes being provided on a surface of the rewiring unit facing toward the evaluation unit and having a smaller second areal distribution compared to the first areal distribution. An areal extent of the evaluation unit is smaller than an areal extent of the converter element.

At least one embodiment of the invention further relates to a medical device having an inventive x-ray detector. The advantages of embodiments of the inventive x-ray detector can advantageously be applied to embodiments of the inventive medical device. The production costs can advantageously be reduced.

According to an embodiment of the invention, the medical device is a computed tomography system. Advantageously, the mechanical stability can satisfy the requirements of a rotating x-ray detector.

At least one embodiment of the invention further relates to a method for producing an x-ray detector, comprising the steps of providing, depositing and connecting. In the providing step, there is provided a converter element comprising a first electrode on a first surface and a pixelated second electrode having a plurality of electrode elements on a second surface and an evaluation unit having pixel electrodes. In the depositing step, a rewiring unit is deposited on the second surface of the converter element, first contacts of electrically conductive connections between the electrode elements and the pixel electrodes being provided and having a first areal distribution on a surface of the rewiring unit facing toward the converter element, and second contacts of the electrically conductive connections between the electrode elements and the pixel electrodes being provided on a surface of the rewiring unit facing toward the evaluation unit and having a smaller second areal distribution compared to the first distribution. In the connecting step, the rewiring unit is connected to the evaluation unit via electrically conductive connections between the second contacts and the pixel electrodes.

BRIEF DESCRIPTION OF THE DRAWINGS

Example embodiments of the invention are explained in more detail below with reference to drawings, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion.

In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a counting x-ray detector having a stack arrangement comprising a converter element, a rewiring unit and an evaluation unit. The converter element has a first electrode on a surface facing away from the evaluation unit and a pixelated second electrode having a plurality of electrode elements on a surface facing toward the evaluation unit. The evaluation unit has pixel electrodes. The rewiring unit is embodied on a surface of the converter element facing toward the evaluation unit, first contacts of electrically conductive connections between the electrode elements and the pixel electrodes being provided on a surface of the rewiring unit facing toward the converter element and having a first areal distribution, and second contacts of the electrically conductive connections between the electrode elements and the pixel electrodes being provided on a surface of the rewiring unit facing toward the evaluation unit and having a smaller second areal distribution compared to the first areal distribution. An areal extent of the evaluation unit is smaller than an areal extent of the converter element.

In at least one embodiment the, in particular direct-converting, planar converter element and the planar evaluation unit are disposed one on top of the other in a stack arrangement, the planar extensions running parallel to one another. The converter element and the evaluation unit can be connected in an electrically conducting manner by way of electrically conductive connections in the rewiring unit and solder joints or adhesive bonds; in particular, the electrode elements and the pixel electrodes can be connected in an electrically conducting manner. The electrically conductive connections between the electrode elements and the pixel electrodes can be substantially equal in length or they can be of different lengths. The solder joints or the adhesive bonds can be embodied in particular between the rewiring unit and the evaluation unit. The solder joints or the adhesive bonds can be embodied between the second contacts and the pixel electrodes.

The rewiring unit can be produced directly on the surface of the converter element facing toward the evaluation unit by way of a lithographic process. The rewiring unit can be embodied directly on the converter element. The rewiring unit can be inseparably connected to the converter element. The connection area becomes smaller in size from the electrode elements toward the pixel electrodes. The areal extent of the evaluation unit can for example be smaller by a factor of 4 than an areal extent of the converter element. The factor can for example assume values in the range of 1.5 to 5.

The first electrode can be embodied as a planar or structured electrode. The pixelated second electrode has a plurality of electrode elements. The number of electrode elements determines the number of pixels or detector elements. A high voltage can be applied between the first electrode and the pixelated second electrode having a plurality of electrode elements, such that the electron-hole pairs released due to the incident x-ray radiation are separated and electrical pulses are registered in the evaluation unit. The high voltage can amount to −1000V, for example. The rewiring unit and the evaluation unit connected to the rewiring unit can be arranged in particular centrally on the converter element.

During operation, the surface of the converter element facing toward the evaluation unit is located on the surface of the converter element facing away from the radiation source. During operation, the surface of the converter element facing away from the evaluation unit is located on the surface of the converter element facing toward the radiation source.

A pixel electrode can be assigned to each electrode element. In particular, each electrode element can be connected in an electrically conducting manner to a pixel electrode via electrically conductive connections of the rewiring unit.

The first contacts of the electrically conductive connections are in electrically conducting connection with the electrode elements. The second contacts of the electrically conductive connections are in electrically conducting connection with pixel electrodes.

The first areal distribution or/and the second areal distribution can also be referred to as the density of the first contacts and second contacts, respectively. In particular, the distances between adjacent first contacts can be greater than the distances between adjacent second contacts. The first areal distribution of the first contacts can substantially correspond to the areal distribution of the electrode elements. The second areal distribution of the second contacts can substantially correspond to the areal distribution of the pixel electrodes. The first contacts can have, in particular in each case, substantially equal areal extents to the electrode elements. The second contacts can have, in particular in each case, substantially equal areal extents to the pixel electrodes. Each pixel electrode can have a smaller areal extent compared to an electrode element. The pixel electrode can for example be smaller by a factor of 4 compared to an electrode element. The factor can lie in the range of 1.5 to 5, for example.

The production costs can advantageously be reduced. Advantageously, an adapter known as an interposer for rerouting wiring can be dispensed with. The surface area of the evaluation unit can advantageously be reduced. The rewiring unit directly on the converter element can advantageously be a low-cost replacement for an interposer for rerouting wiring. The rewiring unit is advantageously mechanically stable, in particular also under temperature variations during operation. The integration density of the x-ray detector can advantageously be increased. Smaller subunits of the x-ray detector can advantageously be realized. The structural complexity of the x-ray detector can advantageously be reduced. Advantageously, a higher flexibility in the relative positioning of the evaluation unit with respect to the converter element can be realized by the decoupling of the pixel structures in the converter element and the evaluation unit. Advantageously, the clearances between adjacent evaluation units or evaluation unit and converter element can be chosen relatively freely.

According to an embodiment of the invention, the electrically conductive connections of the rewiring unit comprise at least one first section perpendicular to a surface normal of the surface of the converter element facing toward the evaluation unit and at least one second section parallel to the surface normal of the surface of the converter element facing toward the evaluation unit. The first areal distribution can be reduced to a smaller second areal distribution via at least the first section and the second section of the electrically conductive connection. Advantageously, the electrode elements can be connected to the pixel electrodes of the evaluation unit, which is smaller compared to the converter element. Advantageously, the rewiring unit comprises an electrically insulating material.

According to an embodiment of the invention, the rewiring unit has at least one electrically insulating layer. The electrically insulating layer can electrically insulate the electrically conductive connections against the converter element, the evaluation unit and adjacent further electrically conductive connections. Advantageously, the electrical signals are not disrupted.

According to an embodiment of the invention, the first section perpendicular to the surface normal of the surface of the converter element facing toward the evaluation unit is at least partially surrounded by the at least one electrically insulating layer or/and the second section parallel to the surface normal of the surface of the converter element facing toward the evaluation unit is at least partially surrounded by the at least one electrically insulating layer or/and a further electrically insulating layer. Particularly advantageously, the first section or/and the second section is/are completely surrounded by the insulating layer or/and a further insulating layer. A rerouting of wiring via the electrically conductive connections can advantageously be embodied within the insulating layer or insulating layers.

According to an embodiment of the invention, the rewiring unit has a metallic intermediate layer. The electric field lines in the converter element are advantageously unaffected by the rewiring unit or the electrically conductive connections of the rewiring unit. The conductor resistance can advantageously be very low. The metallic intermediate layer, if present, can serve as a shield in such a way that the electric field lines in the converter element or the electrical signals are substantially unaffected by the rewiring unit. The shield can be embodied by a plurality of metallic intermediate layers in the rewiring unit.

According to an embodiment of the invention, the rewiring unit has a flexible intermediate layer. The flexible intermediate layer, if present, can minimize mechanical tensions in the x-ray detector, such that signal instabilities are advantageously reduced or avoided. The flexible intermediate layer can be produced as a substep in a lithographic process. The flexible intermediate layer can have a suitable, flexible or soft, in particular electrically insulating, material. The flexible material can compensate for mechanical tensions.

According to an embodiment of the invention, the x-ray detector additionally has a heating element for setting a temperature of the converter element. The temperature of the x-ray detector, in particular of the converter element, can advantageously be stabilized or regulated by the heating element, if present. The heating element can be arranged on the carrier unit, for example. The heating element can be arranged on the first electrode, for example. The heating element can be a Peltier element, for example, or an electrically operable heating loop.

According to an embodiment of the invention, the first electrode is embodied as transparent to visible light, infrared light or ultraviolet light. The first electrode can be transparent in order to enable an additional illumination of the converter element with infrared, ultraviolet or visible light.

According to an embodiment of the invention, the x-ray detector additionally has an illumination unit for illuminating the converter element with visible light, infrared light or ultraviolet light. A polarization state of the converter element can be determined, specified or corrected via the additional illumination.

According to an embodiment of the invention, the first electrode is embodied as nontransparent to visible light, infrared light or ultraviolet light. The first electrode can be nontransparent, in particular to infrared, ultraviolet or visible light.

According to an embodiment of the invention, the x-ray detector additionally has a carrier unit connected to the evaluation unit. Advantageously, the carrier unit can mechanically stabilize the x-ray detector. The carrier unit can be connected to the evaluation unit mechanically and in particular also in an electrically conducting manner, for example via a solder joint or an adhesive bond, such that the signals of the evaluation unit can be conducted away from the x-ray detector via the carrier unit.

According to an embodiment of the invention, the carrier unit is connected at least mechanically to the rewiring unit. The carrier unit can be connected at least mechanically to the converter unit, for example via a solder joint or an adhesive bond. Advantageously, the carrier unit can mechanically stabilize the x-ray detector.

At least one embodiment of the invention further relates to a medical device having an inventive x-ray detector. The advantages of embodiments of the inventive x-ray detector can advantageously be applied to embodiments of the inventive medical device. The production costs can advantageously be reduced.

According to an embodiment of the invention, the medical device is a computed tomography system. Advantageously, the mechanical stability can satisfy the requirements of a rotating x-ray detector.

At least one embodiment of the invention further relates to a method for producing an x-ray detector, comprising the steps of providing, depositing and connecting. In the providing step, there is provided a converter element comprising a first electrode on a first surface and a pixelated second electrode having a plurality of electrode elements on a second surface and an evaluation unit having pixel electrodes. In the depositing step, a rewiring unit is deposited on the second surface of the converter element, first contacts of electrically conductive connections between the electrode elements and the pixel electrodes being provided and having a first areal distribution on a surface of the rewiring unit facing toward the converter element, and second contacts of the electrically conductive connections between the electrode elements and the pixel electrodes being provided on a surface of the rewiring unit facing toward the evaluation unit and having a smaller second areal distribution compared to the first distribution. In the connecting step, the rewiring unit is connected to the evaluation unit via electrically conductive connections between the second contacts and the pixel electrodes.

In an embodiment, the connecting step can include the use of an electrically conductive adhesive or a solder joint. The possible soldering process for connecting the converter element to the evaluation unit via a solder joint advantageously takes place on the rewiring unit, in particular having an insulating layer. The diffusion of solder material into the converter element can advantageously be avoided. A so-called under-bump metallization can advantageously be dispensed with or simplified. The rewiring unit can advantageously reduce tensions by the possible introduction of an underfill. Signal instabilities, also known as drift spots, can advantageously be avoided.

According to an embodiment of the invention, the depositing step comprises a lithographic process. The electrically conductive connections and the insulating layer can advantageously be deposited in a lithographic process.

According to an embodiment of the invention, the depositing step comprises the deposition of at least one insulating layer. The deposition can be accomplished as follows: An insulating layer can be deposited onto the provided converter element, for example via a mask, the electrode elements preferably being left exposed. An electrically conductive material can be deposited onto the exposed electrode elements such that a first contact is produced. A first connection having an electrically conductive material can be deposited onto the insulating layer. A further insulating layer can subsequently be deposited via a further mask, at least one point being left exposed for contacting the second connection. Starting from the point left exposed, the second connection is formed via an electrically conductive material. Starting from the second connection, the third connection, the end of which is the second contact, is formed via an electrical material. Optionally, an additional insulating layer can be deposited which at least partially touches the evaluation unit after the connection is made.

According to an embodiment of the invention, the depositing step comprises the deposition of a metallic intermediate layer or/and a flexible intermediate layer. The metallic intermediate layer or/and the flexible intermediate layer can be deposited in particular onto an insulating intermediate layer. The metallic intermediate layer can in particular be electrically insulated from the electrically conductive connection. The electrically conductive connections can extend through the metallic intermediate layer or the flexible intermediate layer, such that a continuous electrically conductive connection is formed.

Figure 1:
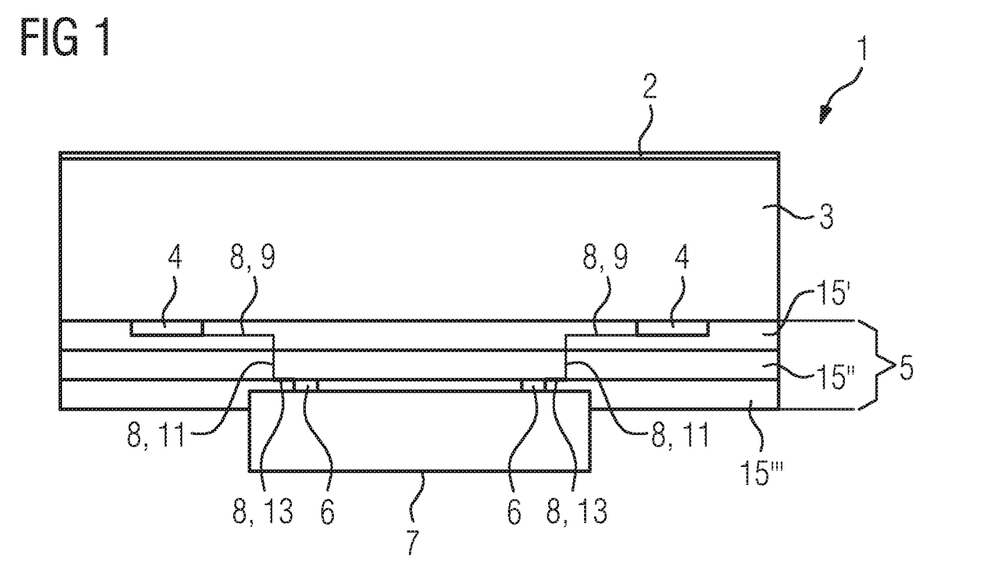
FIG. 1 schematically shows an inventive x-ray detector in a first embodiment variant.

FIG. 1 shows an example embodiment of the inventive x-ray detector 1 in a first embodiment variant. The x-ray detector 1 has a stack arrangement comprising a converter element 3, a rewiring unit 5 and an evaluation unit 7. The converter element 3 has a first electrode 2 on a surface facing away from the evaluation unit 7 and a pixelated second electrode having a plurality of electrode elements 4 on a surface facing toward the evaluation unit 7. The evaluation unit 7 has pixel electrodes 6. The rewiring unit 5 is embodied on a surface of the converter element 3 facing toward the evaluation unit 7, first contacts of electrically conductive connections 8, 9, 11, 13 between the electrode elements 4 and the pixel electrodes 6 being provided on a surface of the rewiring unit 5 facing toward the converter element 3 and having a first areal distribution, and second contacts of the electrically conductive connections 8, 9, 11, 13 between the electrode elements 4 and the pixel electrodes 6 being provided on a surface of the rewiring unit 5 facing toward the evaluation unit 7 and having a smaller second areal distribution compared to the first areal distribution. An areal extent of the evaluation unit 7 is smaller than an areal extent of the converter element 3.

The electrically conductive connections 8, 9, 11, 13 of the rewiring unit 5 comprise at least one first section 9 perpendicular to a surface normal of the surface of the converter element 3 facing toward the evaluation unit 7 and at least one second section 11 parallel to the surface normal of the surface of the converter element 3 facing toward the evaluation unit 7. The rewiring unit 5 has electrically insulating layers 15', 15'', 15'''.

The first section 9 perpendicular to the surface normal of the surface of the converter element 3 facing toward the evaluation unit 7 is at least partially surrounded by the at least one electrically insulating layer 15' or/and the second section 11 parallel to the surface normal of the surface of the converter element 3 facing toward the evaluation unit 7 is at least partially surrounded by the at least one electrically insulating layer 15' and further electrically insulating layers 15", 15'".

Figure 2:
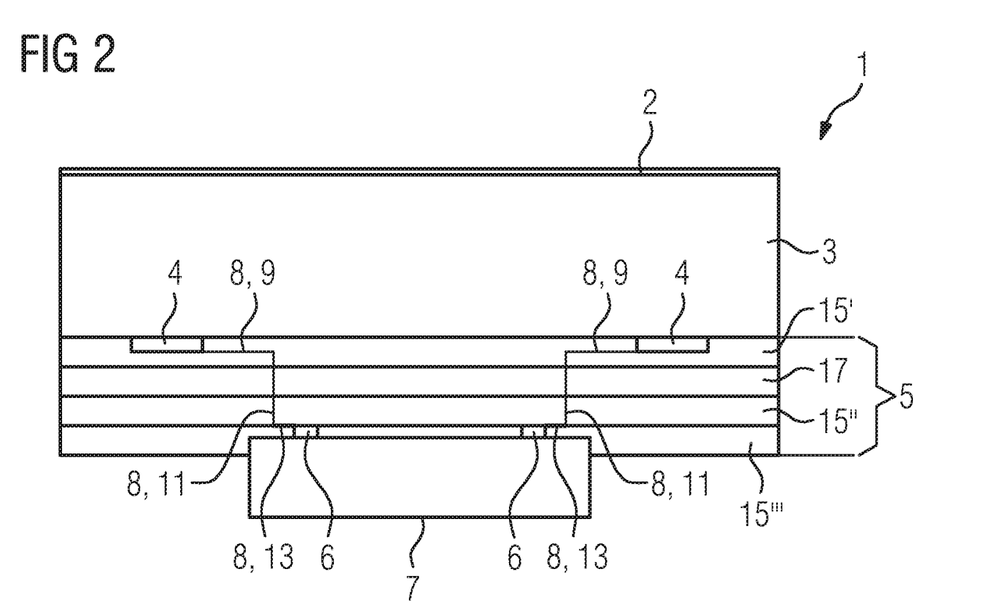
FIG. 2 schematically shows an inventive x-ray detector in a second embodiment variant.

FIG. 2 shows an example embodiment of the inventive x-ray detector 1 in a second embodiment variant. The rewiring unit 5 has a metallic intermediate layer 17.

Figure 3:
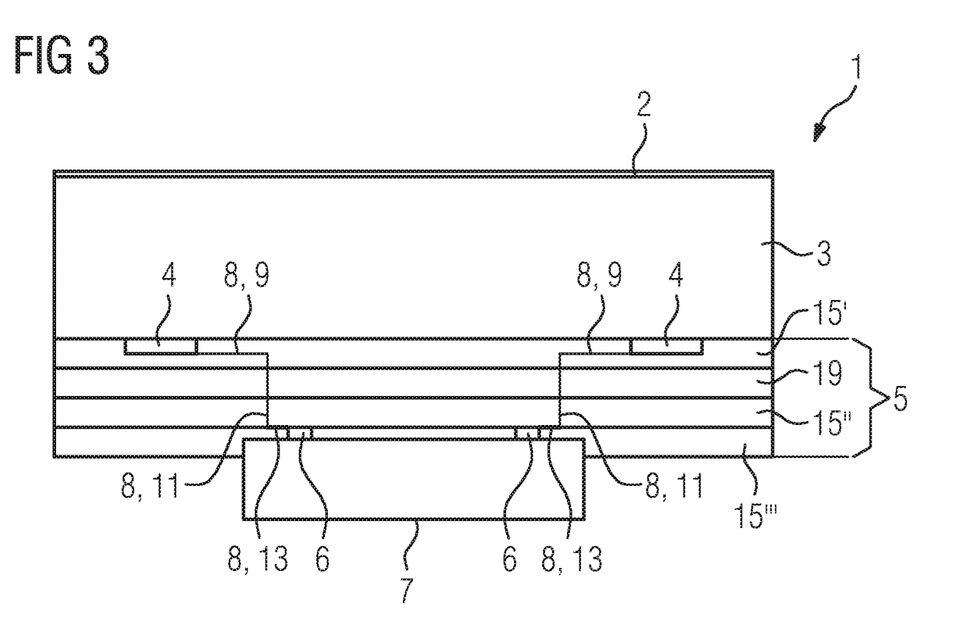
FIG. 3 schematically shows an inventive x-ray detector in a third embodiment variant.

FIG. 3 shows an example embodiment of the inventive x-ray detector 1 in a third embodiment variant. The rewiring unit 5 has a flexible intermediate layer 19.

Figure 4:
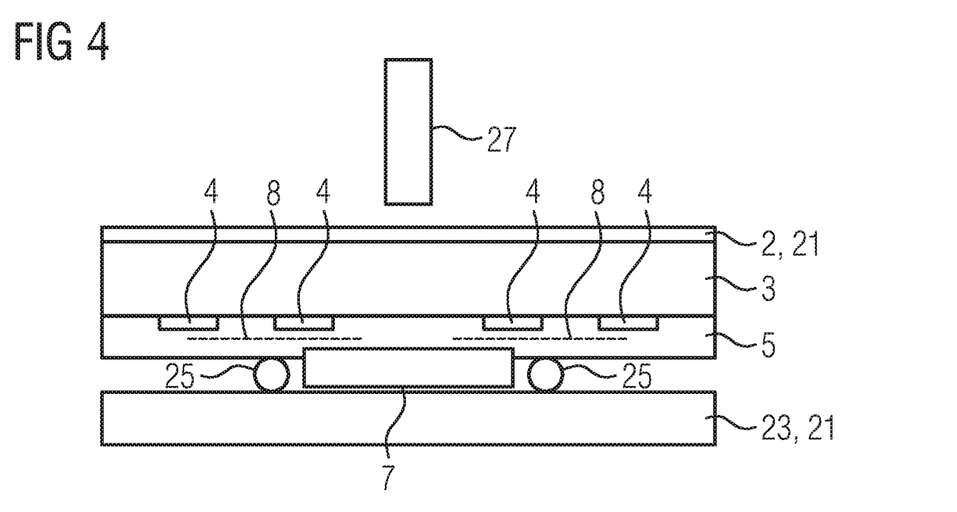
FIG. 4 schematically shows an inventive x-ray detector in a fourth embodiment variant.

FIG. 4 shows an example embodiment of the inventive x-ray detector 1 in a fourth embodiment variant. The x-ray detector 1 additionally has a carrier unit 23 connected to the evaluation unit 7. The x-ray detector 1 additionally has a heating element 21 for setting a temperature of the converter element 3. The heating element 21 is incorporated in the carrier unit 23 or/and in the first electrode 2. The carrier unit 23 is connected at least mechanically to the rewiring unit 5 via solder joints 25. The x-ray detector 1 additionally has an antiscatter grid 27. Only one grid wall of the antiscatter grid 27 is depicted schematically.

Figure 5:
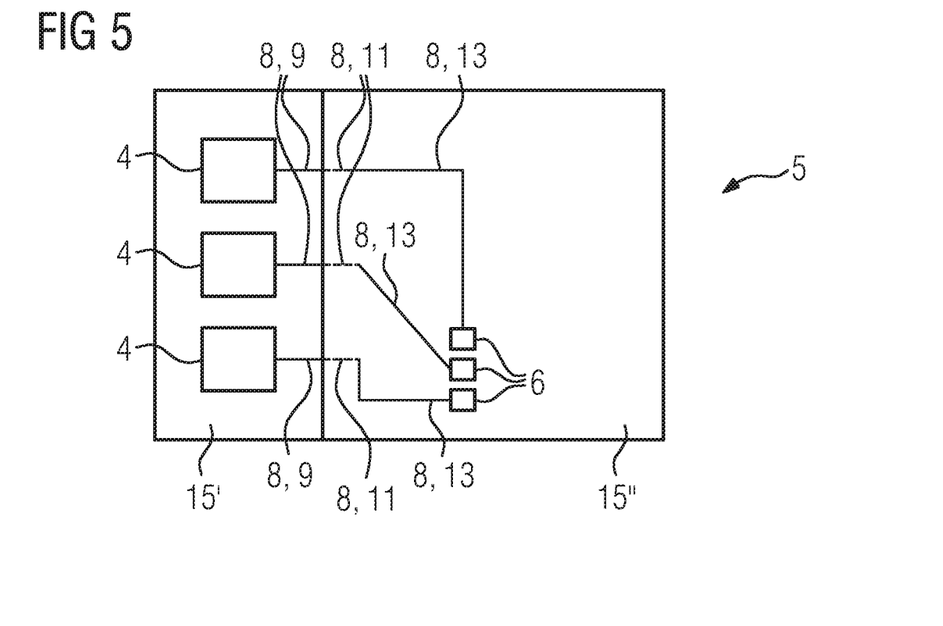
FIG. 5 schematically shows a rewiring unit of an embodiment of the inventive x-ray detector in a plan view.

FIG. 5 shows an example embodiment of a rewiring unit 5 of the inventive x-ray detector 1 in a plan view. The areal extent of the insulating layer 15' is greater than the areal extent of the insulating layer 15". The first connection 8,9 extends over the surface of the insulating layer 15'. The second connection 8, 11 connects the first connection 8, 9 to the third connection 8, 13. The third connection 8, 13 extends over the surface of the insulating layer 15". The pixel electrodes 6 have a smaller areal extent than the electrode elements 4.

Figure 6:
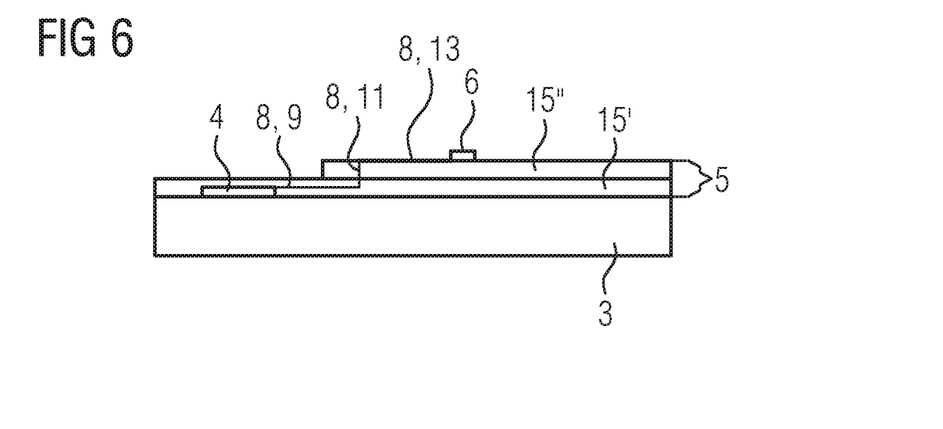
FIG. 6 schematically shows a rewiring unit of an embodiment of the inventive x-ray detector in a side view.

FIG. 6 shows an example embodiment of a rewiring unit 5 directly on the converter element 3 of the inventive x-ray detector 1 in a side view.

Figure 7:
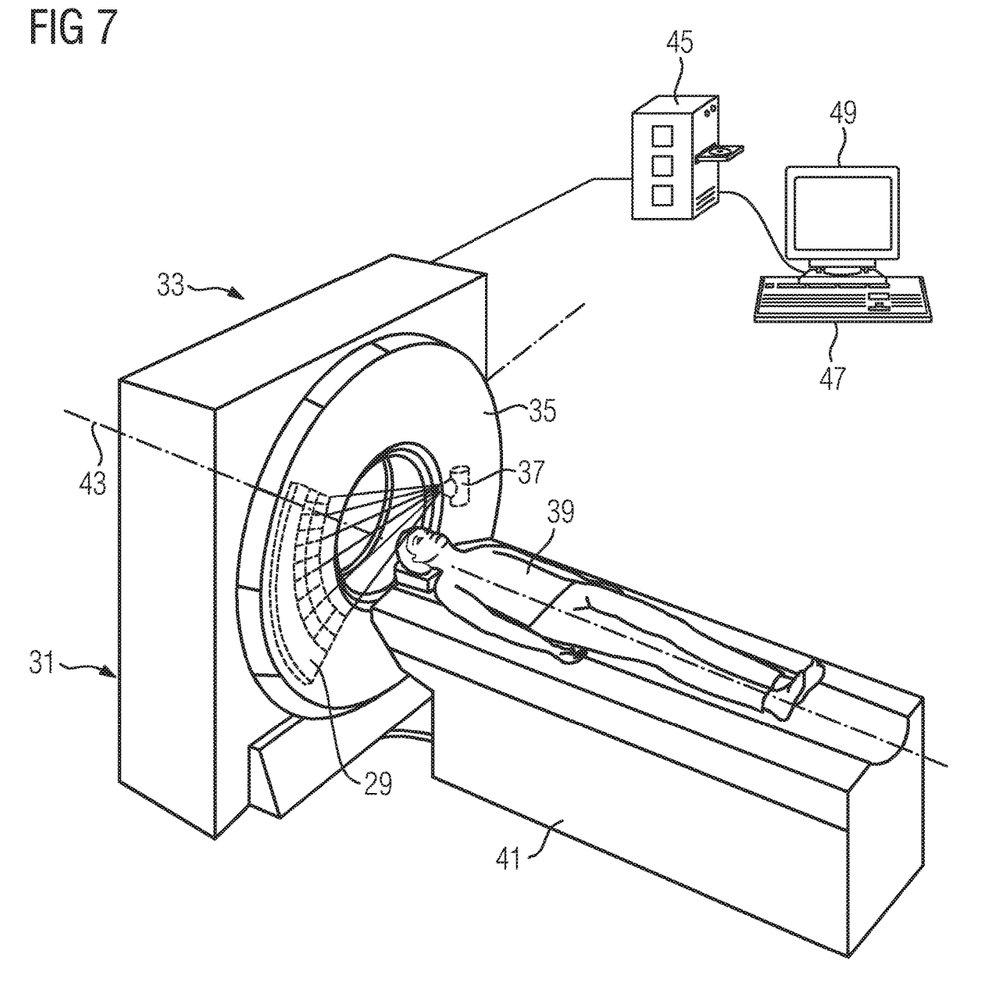
FIG. 7 schematically shows a view of an embodiment of an inventive computed tomography system.

FIG. 7 shows an example embodiment of an inventive computed tomography system 31 having an inventive x-ray detector. The computed tomography system 31 includes a gantry 33 with a rotor 35. The rotor 35 comprises an x-ray source 37 and a detector device 29 having at least one inventive x-ray detector. The patient 39 is supported on the patient couch 41 and is movable through the gantry 33 along the axis of rotation z 43. A computing unit 45 is used for controlling and calculating the slice images. An input device 47 and an output device 49 are connected to the computing unit 45.

Figure 8:
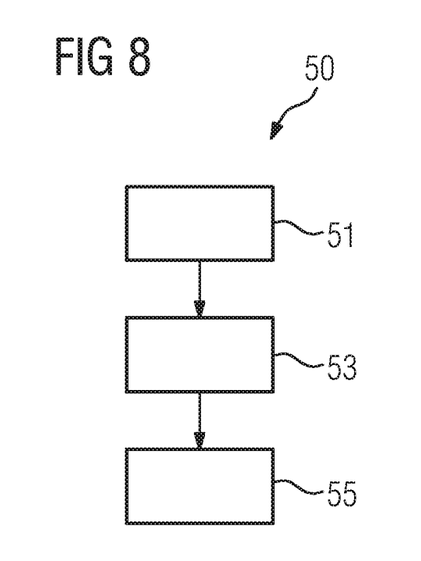
FIG. 8 schematically shows a flowchart of an embodiment of the inventive method.

FIG. 8 shows an example schematic flowchart of the inventive method 50 for producing an x-ray detector, comprising the steps of providing 51, depositing 53 and connecting 55. In the providing step 51, a converter element having a first electrode on a first surface and a pixelated second electrode having a plurality of electrode elements on a second surface is provided and an evaluation unit having pixel electrodes is provided. In the depositing step 53, a rewiring unit is deposited on the second surface of the converter element, first contacts of electrically conductive connections between the electrode elements and the pixel electrodes being provided and having a first areal distribution on a surface of the rewiring unit facing toward the converter element, and second contacts of the electrically conductive connections between the electrode elements and the pixel electrodes being provided on a surface of the rewiring unit facing toward the evaluation unit and having a smaller second areal distribution compared to the first distribution. The depositing step 53 comprises a lithographic process. In the connecting step 55, the rewiring unit is connected to the evaluation unit via electrically conductive connections between the second contacts and the pixel electrodes.

Although the invention has been illustrated in greater detail on the basis of the preferred example embodiment, the invention is not limited by the disclosed examples, and other variations can be derived herefrom by the person skilled in the art without leaving the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An x-ray detector having a stack arrangement, comprising:
   an evaluation unit including pixel electrodes;
   a converter element including a first electrode on a surface of the converter element facing away from the evaluation unit and a pixelated second electrode including a plurality of electrode elements on a surface of the converter element facing toward the evaluation unit, an areal extent of the evaluation unit being relatively smaller than an areal extent of the converter element; and
   a rewiring unit, having a metallic intermediate layer, embodied on a surface of the converter element facing toward the evaluation unit,
      first contacts of electrically conductive connections of the rewiring unit between the plurality of electrode elements and the pixel electrodes being provided on a surface of the rewiring unit facing toward the converter element, including a first areal distribution, and
      second contacts of the electrically conductive connections between the plurality of electrode elements and the pixel electrodes being provided on a surface of the rewiring unit facing toward the evaluation unit, including a relatively smaller second areal distribution compared to the first areal distribution, wherein the metallic intermediate layer is electrically insulated from the electrically conductive connections.

2. The x-ray detector of claim 1, wherein the electrically conductive connections of the rewiring unit include at least one first section perpendicular to a surface normal of the surface of the converter element facing toward the evaluation unit and at least one second section parallel to the surface normal of the surface of the converter element facing toward the evaluation unit.

3. The x-ray detector of claim 1, wherein the rewiring unit includes at least one electrically insulating layer.

4. The x-ray detector of claim 2, wherein at least one of the at least one first section is at least partially surrounded by at least one electrically insulating layer and the at least one second section is at least partially surrounded by at least one electrically insulating layer.

5. The x-ray detector of claim 1, wherein the rewiring unit includes a flexible intermediate layer.

6. The x-ray detector of claim 1, further comprising:
a heating element to set a temperature of the converter element.

7. The x-ray detector of claim 1, further comprising:
a carrier unit connected to the evaluation unit.

8. The x-ray detector of claim 7, wherein the carrier unit is connected at least mechanically to the rewiring unit.

9. A medical device comprising:
an x-ray detector of claim 1.

10. The medical device of claim 9, wherein the medical device is a computed tomography system.

11. A method for producing an x-ray detector, comprising:
providing a converter element including a first electrode on a first surface of the converter element and a pixelated second electrode including a plurality of electrode elements on a second surface of the converter element, and providing an evaluation unit including pixel electrodes;
depositing a rewiring unit on the second surface of the converter element, first contacts of electrically conductive connections between the plurality of electrode elements and the pixel electrodes being provided, including a first areal distribution on a surface of the rewiring unit facing toward the converter element, and second contacts of the electrically conductive connections between the plurality of electrode elements and the pixel electrodes being provided on a surface of the rewiring unit facing toward the evaluation unit, including a relatively smaller second areal distribution compared to the first areal distribution, wherein the depositing includes deposition of a metallic intermediate layer;
connecting the rewiring unit to the evaluation unit via electrically conductive connections between the second contacts, of the electrically conductive connections between the plurality of electrode elements and the pixel electrodes, and the pixel electrodes to produce the x-ray detector; and
electrically insulating the metallic intermediate layer from the electrically conductive connections.

12. The method of claim 11, wherein the depositing includes a lithographic process.

13. The method of claim 11, wherein the depositing includes deposition of at least one insulating layer.

14. The x-ray detector of claim 2, wherein the rewiring unit includes at least one electrically insulating layer.

15. The x-ray detector of claim 14, wherein at least one of
the at least one first section is at least partially surrounded by the at least one electrically insulating layer, and
the at least one second section is at least partially surrounded by the at least one electrically insulating layer or a further electrically insulating layer.

16. The x-ray detector of claim 1, wherein
at least one first section, of the electrically conductive connections of the rewiring unit, is at least partially surrounded by the at least one electrically insulating layer, and
at least one second section, the electrically conductive connections of the rewiring unit, is at least partially surrounded by the at least one electrically insulating layer or a further electrically insulating layer.

17. The x-ray detector of claim 2, further comprising:
a heating element to set a temperature of the converter element.

18. The x-ray detector of claim 3, further comprising:
a heating element to set a temperature of the converter element.

19. A medical device comprising:
an x-ray detector of claim 2.

20. A medical device comprising:
an x-ray detector of claim 3.

21. A medical device comprising:
an x-ray detector of claim 4.

22. The method of claim 12, wherein the depositing includes deposition of at least one insulating layer.

23. The method of claim 12, wherein the depositing includes deposition of at least one of a metallic intermediate layer or a flexible intermediate layer.

24. The method of claim 13, wherein the depositing includes deposition of at least one of a metallic intermediate layer or a flexible intermediate layer.

25. The x-ray detector of claim 1, wherein the metallic intermediate layer is sandwiched between electrical insulating layers of the rewiring unit.

26. The method of claim 11, wherein the metallic intermediate layer is sandwiched between electrical insulating layers of the rewiring unit.

* * * * *